(12) United States Patent
Song et al.

(10) Patent No.: US 12,376,729 B2
(45) Date of Patent: Aug. 5, 2025

(54) ENDOSCOPIC SURGERY SYSTEM WITH AUTOMATIC HYDRAULIC MONITORING FUNCTION

(71) Applicants: JIANGXI INVENTOR TECHNOLOGY CO., LTD., Jiangxi (CN); SHENZHEN INVENTOR TECHNOLOGY CO., LTD., Guangdong (CN)

(72) Inventors: Yang Song, Jiangxi (CN); Shaorong Li, Jiangxi (CN); Haibin Fan, Jiangxi (CN)

(73) Assignees: JIANGXI INVENTOR TECHNOLOGY CO., LTD., Ganzhou (CN); SHENZHEN INVENTOR TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 19/012,968

(22) Filed: Jan. 8, 2025

(65) Prior Publication Data

US 2025/0143540 A1 May 8, 2025

Related U.S. Application Data (63) Continuation of application No. PCT/CN2024/131450, filed on Nov. 12, 2024.

(30) Foreign Application Priority Data

Sep. 26, 2023 (CN) .......................... 202311245926.2

(51) Int. Cl.
 *A61B 1/00* (2006.01)
 *A61B 1/015* (2006.01)
(Continued)

(52) U.S. Cl.
 CPC .......... *A61B 1/00006* (2013.01); *A61B 1/015* (2013.01); *A61B 18/26* (2013.01);
 (Continued)

(58) Field of Classification Search
 CPC ..... A61B 1/00006; A61B 1/015; A61B 50/13; A61B 18/26; A61B 2090/064; A61B 2018/00982; G16H 40/63
 (Continued)

(56) References Cited

U.S. PATENT DOCUMENTS

2014/0066888 A1 3/2014 Parikh et al.
2016/0256629 A1 9/2016 Grosman et al.
(Continued)

FOREIGN PATENT DOCUMENTS

CA 2884999 A1 3/2014
CN 104014036 A 9/2014
(Continued)

OTHER PUBLICATIONS

1st Office Action of counterpart Chinese Patent Application No. 202311245926.2 issued on Sep. 29, 2024.
(Continued)

*Primary Examiner* — Anh Tuan T Nguyen
*Assistant Examiner* — James Edward Boice (57) ABSTRACT

Provided is an endoscopic surgery system with automatic hydraulic monitoring function, comprising a control system, a cart kit and an endoscope accessory. Then control system includes a processor, a touch display, a perfusion pump, a negative pressure pump, etc. The cart kit includes a cart, a perfusion tube and an extraction tube. The endoscope accessory includes a pressure measuring guide sheath, a hydraulic sensor and an electron microscope. When the endoscope is employed for observation, the invention can control the perfusion and monitoring of the liquid in endoscope instru-
(Continued)

ment, as well as the cavity liquid pressure in organs, allowing for precise control of the intracavity pressure during operation. The real-time monitoring module measures the liquid pressure in the organ in real time and sends data to the control system, calculates a state of the intracavity pressure based on real-time data obtained from the hydraulic sensor using intelligent PID control.

9 Claims, 2 Drawing Sheets

(51) Int. Cl.
 A61B 18/26 (2006.01)
 A61B 50/13 (2016.01)
 G16H 40/63 (2018.01)
 A61B 18/00 (2006.01)
 A61B 90/00 (2016.01)

(52) U.S. Cl.
 CPC .............. *A61B 50/13* (2016.02); *G16H 40/63* (2018.01); *A61B 2018/00982* (2013.01); *A61B 2090/064* (2016.02)

(58) Field of Classification Search
 USPC ........................................................ 600/108
 See application file for complete search history.

(56) References Cited

U.S. PATENT DOCUMENTS

| | | | |
|---|---|---|---|
| 2016/0279329 | A1 | 9/2016 | Faisal et al. |
| 2018/0110948 | A1 | 4/2018 | Dellaca et al. |
| 2019/0134279 | A1 | 5/2019 | Benamou et al. |
| 2023/0285657 | A1* | 9/2023 | Kazuno .................. A61M 1/72 |

FOREIGN PATENT DOCUMENTS

| | | |
|---|---|---|
| CN | 106312397 A | 1/2017 |
| CN | 103767744 B | 3/2017 |
| CN | 207186605 U | 4/2018 |
| CN | 108066870 A | 5/2018 |
| CN | 208653701 U | 3/2019 |
| CN | 112274097 A | 1/2021 |
| CN | 113509221 A | 10/2021 |
| CN | 116549749 A | 8/2023 |
| WO | 2023279434 A1 | 1/2023 |

OTHER PUBLICATIONS

First Search Report of counterpart Chinese Patent Application No. 202311245926.2 issued on Sep. 26, 2024.
Notice of Allowance of counterpart Chinese Patent Application No. 202311245926.2 issued on Oct. 29, 2024.
Supplementary Search Report of counterpart Chinese Patent Application No. 202311245926.2 issued on Oct. 22, 2024.
Xiaoping, Jiang, Intelligent PID Control of Hydraulic Servo System, China's Distinction Master Dissertations Full-text Database (Engineering Science and Technology II), Dec. 1, 2002.
Jianbo, Zhou, Design of automatic sampling system for blood group analysis, China's Distinction Master Dissertations Full-text Database (Engineering Science and Technology II), Jun. 1, 2022.

* cited by examiner

ENDOSCOPIC SURGERY SYSTEM WITH AUTOMATIC HYDRAULIC MONITORING FUNCTION

CROSS REFERENCE TO RELATED APPLICATIONS

The present application is a Continuation Application of PCT Application No. PCT/CN2024/131450 filed on Nov. 12, 2024, which claims the benefit of Chinese Patent Application No. 202311245926.2 filed on Sep. 26, 2023. All the above are hereby incorporated by reference in their entirety.

TECHNICAL FIELD

The invention belongs to the field of medical instrument technology and intelligent medical treatment, in particular to an endoscopic surgery system with automatic hydraulic monitoring function.

BACKGROUND

Endoscopic diagnosis and treatment technology refers to a technology of establishing a channel through the natural cavity of human body or percutaneous to the organ cavity, and placing an endoscope into a certain organ cavity of a patient for diagnosis and treatment. Endoscope is used for observation and treatment in a narrow body cavity or hole, it needs to be continuously perfused with normal saline to keep the endoscope clear. Some specific endoscopic diagnosis and treatment operations also have specific requirements on the amount of liquid perfusion and the circulation speed in cavity, so as to achieve specific purposes and effects, such as eliminating the soft tissue damage caused by the heat energy of holmium laser lithotripsy, improving the visual field definition under the condition of lithotripsy or bleeding, and taking the cavity samples out of the body by liquid circulation, etc. Due to different functions and structures, all organs of human body have their own physiological pressures. If the amount of liquid perfused into the cavity is too large or the liquid outlet channel is blocked, the liquid pressure in cavity will increase. When the pressure exceeds the limit value, the liquid in cavity, bacterial toxins and pathological tissues will flow back through the interstitial space, lymphatic system and venous system, leading to various complications. At present, all kinds of conventional endoscopic diagnosis and treatment techniques, using the existing domestic and foreign surgical instruments and liquid perfusion & extraction equipment, can not accurately perform perfusion with the required amount of liquid during operation, let alone monitor and effectively control the liquid pressure in cavity.

Perfusion pump is a kind of pump that uses liquid medium to pressurize and expand the cavity to form a visible space, and can clean the blood in cavity. Usually, perfusion tube is connected to an endoscope for perfusion, which makes the field of vision clearer during endoscopic observation and operation. Negative pressure pump is a vacuum pump set as a negative pressure source, which makes the pipeline of the extraction system reach the required negative pressure value through the extraction of the vacuum pump, and is used to suck sputum, blood, pus, perfusion liquid and other pollutants in patient's body. Guide sheath refers to a catheter used to assist endoscope and surgical instruments to enter the body cavity, i.e., to establish a channel through natural cavity or percutaneous puncture, and the catheter can also be connected with a extraction device.

In the prior art, the above-mentioned perfusion pump, negative pressure pump, guide sheath, etc. are all separate units, and a system is formed by installing induction elements in the corresponding independent units. For example, patent application (CN201821477696.7) discloses a pressure measuring endoscope and a pressure detection system including the pressure measuring endoscope, while patent application (CN201720092860.1) discloses a pressure measuring endoscope including an endoscope and a pressure measuring device for detecting the pressure in cavity. Patent application (CN201410041761.1) discloses a medical perfusion and extraction platform, which includes a main control unit, a perfusion device, a extraction device and a feedback device. The perfusion pump introduces physiological saline into human organs, while negative pressure pump draws it out. The hydraulic sensor detects the pressure in organ, so that when the pressure reaches a predetermined value, the main control unit adjusts the speed of perfusion and extraction.

However, the above patent applications all employ relatively independent pressure measuring devices to the endoscope system or perfusion and extraction system, which can not achieve good cooperation and data sharing.

In view of this, the present application aims to provide an endoscopic surgery system with automatic hydraulic monitoring function, which skillfully integrates a liquid perfusion device, a liquid extraction device, a liquid pressure monitoring and control device and a surgical endoscope, and can realize real-time data sharing and excellent cooperation. Specifically, when the endoscope is employed for observation, the invention can control the perfusion and monitoring of the liquid in endoscope instrument, as well as the cavity liquid pressure in organs (such as renal pelvis, uterine cavity, biliary tract system, etc.), allowing for precise control of the intracavity pressure during operation. According to different requirements of endoscopic surgery, sufficient liquid circulation can be achieved, the visual field in cavity can be kept clear, the holmium laser heat can be quickly taken away, and the samples in cavity can be removed by extraction. More importantly, the hydraulic sensor of the application also has an intelligent identification function, which can guarantee the quality, sensing efficiency, sensing accuracy and use stability of the hydraulic sensor, thereby improving the safety of the invention.

SUMMARY OF THE INVENTION

In order to address the above issues, the present application provides an endoscopic surgery system with automatic hydraulic monitoring function, which skillfully integrates a liquid perfusion device, a liquid extraction device, a liquid pressure monitoring and control device and a surgical endoscope, and can realize real-time data sharing and excellent cooperation. Specifically, when the endoscope is employed for observation, the invention can control the perfusion and monitoring of the liquid in endoscope instrument, as well as the cavity liquid pressure in organs (such as renal pelvis, uterine cavity, biliary tract system, etc.), allowing for precise control of the intracavity pressure during operation. According to different requirements of endoscopic surgery, sufficient liquid circulation can be achieved, the visual field in cavity can be kept clear, the holmium laser heat can be quickly taken away, and the samples in cavity can be removed by extraction. More importantly, the hydraulic sensor of the application also has an intelligent identification function, which can guarantee the quality, sensing efficiency, sensing accuracy and use stability of the hydraulic sensor, thereby improving the safety of the invention.

In order to solve the above problems, the invention proposes the following technical solutions.

An endoscopic surgery system with automatic hydraulic monitoring function is provided, including a control system, a cart kit and an endoscope accessory; the control system includes a processor, and a touch display, a perfusion pump and a negative pressure pump connected with the processor; the cart kit includes a cart, a perfusion tube and a extraction tube; the endoscope accessory includes a pressure measuring guide sheath, a hydraulic sensor and an electronic endoscope; the hydraulic sensor is a sensor with a recognition function; the perfusion tube is powered by the perfusion pump, and the perfusion tube is connected with a perfusion channel of the electronic endoscope; the electronic endoscope is arranged in the pressure measuring guide sheath, and the pressure measuring guide sheath is connected with an end of the extraction tube and a piezometric tube of the hydraulic sensor, another end of the extraction tube is provided with a extraction power by the negative pressure pump, and the hydraulic sensor is connected with the processor via the hydraulic sensor interface and the hardware processing module in turn.

As an improvement of the endoscopic surgery system with automatic hydraulic monitoring function, the hydraulic sensor includes a programmable read-only memory, an output impedance and an input impedance; the output impedance is connected in parallel with the programmable read-only memory, and both the output impedance and the input impedance are detachably connected with a hydraulic sensor interface; the input impedance is connected with DC power supply via the hydraulic sensor interface and a sampling resistor, and a sampling resistor voltage outputs signals to the processor through a first analog-to-digital conversion module; the output impedance is connected with a second analog-to-digital conversion module and the processor via the hydraulic sensor interface, and the second analog-to-digital conversion module outputs signals to the processor.

As an improvement of the endoscopic surgery system with automatic hydraulic monitoring function, a memory content of the programmable read-only memory includes a preamble code, time, serial number, flag bit and checksum; the preamble code is a frame header of the memory content, the time is the first recorded time, the serial number is an unique identification code of the hydraulic sensor, the flag bit is an insertion state of the recorded hydraulic sensor, and the function of the checksum is to verify the completeness of the preamble code, time, serial number and flag bit.

As an improvement of the endoscopic surgery system with automatic hydraulic monitoring function, an identification function of the hydraulic sensor includes:

a) identification of line sequence errors and whether access is granted: when the hydraulic sensor is not connected to the sensor interface, the sensor interface is open-circuited, and a sampling voltage of the sampling resistor is zero volts, thus it is determined that the hydraulic sensor is not connected; when the hydraulic sensor is connected to the sensor interface, a sampling voltage corresponding to the sampling resistor voltage is obtained, thus it is determined that the hydraulic sensor is connected and whether the line sequence of the connected hydraulic sensor is correct;

b) identification of sensor matching: when the hydraulic sensor is inserted into the sensor interface, the processor compares the identification code in the system with the unique serial number stored in the programmable read-only memory, and if they are the same, they match, and if they are different, they do not match; and c) identification of whether the sensor is used for the second time: a real-time clock circuit is arranged in the processor; when the hydraulic sensor is inserted into the sensor interface, the processor reads the flag bit in the programmable read-only memory and determines whether the flag bit record is inserted for the first time; if yes, the current time is written into the programmable read-only memory and the status of the flag bit is changed; if no, the processor reads the time stored in the programmable read-only memory and compares it with the current time, and if it exceeds the time limit, it is regarded as secondary use.

As an improvement of the endoscopic surgery system with automatic hydraulic monitoring function, the electronic endoscope is a soft electronic endoscope or a hard electronic endoscope, and the electronic endoscope is a catheter with a camera, and is provided with a control button. The control button can control the start and stop of the perfusion pump and adjust the perfusion amount.

As an improvement of the endoscopic surgery system with automatic hydraulic monitoring function, the materials of the perfusion tube and the extraction tube are silica gel.

As an improvement of the endoscopic surgery system with automatic hydraulic monitoring function, the processor is an embedded processor and runs CFR (Core Full Register) embedded underlying software.

The processor is provided with a USB interface, a digital-analog video interface, a real-time monitoring module, a data memory module, a sound-light alarm module, a hardware processing module and an encoding & decoding module; wherein an input end of the encoding & decoding module is connected with an electronic endoscope interface, an input end of the electronic endoscope interface is connected with the electronic endoscope, and an output end of the encoding & decoding module is connected with the processor; wherein the real-time monitoring module is used for monitoring the pressure of liquid in an organ in real time and providing data to the control system, so as to realize accurate control of intracavity pressure during operation, and the real-time monitoring module includes a plurality of high-precision hydraulic sensors, these sensors are arranged in the organ and close to an operation area so as to measure the pressure of liquid in the organ; the hydraulic sensor transmits real-time pressure data to the control system through a data line connected to the control system or a wireless communication mode, calculates a state of the intracavity pressure based on real-time data obtained from the hydraulic sensor using intelligent PID control, and adjusts a perfusion and extraction speed of the liquid according to a given target pressure, so as to maintain the intracavity pressure in a safe range, details are as follows:

pressure change of a cavity liquid is expressed by the following difference equation:

$$P(t+1) = P(t) + \Delta P_{in} - \Delta P_{out}$$

wherein, $\Delta P_{in}$ is the pressure change caused by liquid perfusion, $\Delta P_{out}$ is the pressure change caused by liquid extraction, P(t) represents a pressure at time t, and P(t+1) represents a pressure at time t(t+1); suppose there are an exploration factors, and a position and speed of each exploration factor represent a parameter value of a control strategy, in each iteration, the position and speed of each exploration factor are updated, and a fitness value is calculated; wherein a parameter of the control strategy is represented by d dimensions, each dimension corresponds to a control parameter, and the control strategy is expressed as d dimension vector X, where X=(X$_1$, X$_2$, . . . , X$_d$), X$_1$ represents a value of the first dimension parameter, X$_2$ represents a value of the second dimension parameter, and X$_d$ represents a value of the d$_{th}$ dimension parameter, and an objective function H(X) is defined and used for evaluating performance of each exploration factor, H(X) is expressed as follows:

$$H(X) = w_1 \epsilon(X) + w_2 k(X_{in} + X_{out})$$

$\epsilon$ represents pressure control error, X$_{in}$ represents liquid perfusion speed parameter, X$_{out}$ represents liquid extraction speed parameter, k(X$_{in}$+X$_{out}$) represents energy consumption, that is, the energy required for liquid flow caused by the control strategy, k is a constant related to the energy consumption per fluid speed unit, w$_1$ and w$_2$ are parameters for balancing weight of the pressure control error and the energy consumption; a fitness function A(X) is defined as H(X), and the objective function includes pressure control error and energy consumption: A(X)=−H(X), and a position update model of each exploration factor i is expressed by:

$$X_i(t+1) = X_i(t) + \Delta X_i(t+1)$$

X$_i$(t) represents the position of the exploration factor i at time t, and is a d dimension vector; $\Delta$X$_i$(t+1) represents a position variance of the exploration factor i at time t+1, and the speed update model of each exploration factor i is expressed by:

$$V_i(t+1) = V_i(t) + \Delta V_i(t+1)$$

V$_i$(t) represents a speed of the exploration factor i at time t, corresponds to the position update, and is a d dimensional vector; $\Delta$V$_i$(t+1) represents a speed variance of the exploration factor i at time t+1; the position and speed of the exploration factors i are coordinated and adjusted through information exchange, and the information exchange is expressed by the following model:

$$\Delta X_i(t+1) = H_1(X_i(t), X_{neighbor_i}(t), t) \int_{T_0}^{T^*} X_i(t) X_{neighbor_i}(t+l) dt +$$

$$- \sum_{i=1}^{N} pr(X_i(t)) \log(pr(X_i(t))) H_2(X_i(t), t)$$

$\Delta V_i(t+1) =$ $$\gamma H_3(X_i(t), V_i(t), X_{neighbor_i}(t), t) + H_4(X_i(t), V_i(t), t) \int_{T_0}^{T^*} X_i(t) V_i(t+l) dt$$

X$_{neighbor_i}$(t) represents the position of the neighbor exploration factor i at time t, $\Delta$X$_i$(t+1) and $\Delta$V$_i$(t+1) are variations of position and speed, used for updating the position and speed respectively, $\gamma$ is an adjustment parameter, and affects weight of the information exchange, T$_0$ represents an initial time of statistics, T* represents an ending time of statistics, H$_1$(X$_i$(t), X$_{neighbor_i}$(t),t) and H$_2$(X$_i$(t),t) are information exchange functions of the neighboring exploration factor, used for adjusting the position, H$_3$(X$_i$(t), V$_i$(t),X$_{neighbor_i}$(t),t) and H$_4$(X$_i$(t), V$_i$(t),t) are information exchange functions of the neighboring exploration factor, used for adjusting the speed, to indicate the information exchange function with the adjacent exploration factor, l is lag time, and pr is a probability function.

As an improvement of the endoscopic surgery system with automatic hydraulic monitoring function, a dynamic behavior of liquid perfusion and extraction and a response of pressure are expressed by the following formula:

$$\dot{P} = \frac{Q_{in}(t) - Q_{out}(t)}{V}$$

wherein, $\dot{P}$(t) represents a change rate of pressure, Q$_{in}$(t) represents a liquid perfusion rate at time t, Q$_{out}$(t) represents a liquid extraction rate at time t, V represents a volume of the cavity, and the objective function J(t) is defined as:

$$J(t) = \frac{1}{2}(P_{objective} - P(t))^2$$

it represents a performance index pursued by the system, the objective function is the difference between the intracavity pressure and the target pressure, i.e., P(t) is the pressure at time t, P$_{objective}$ is the expected target pressure, and an output of a PID control algorithm is expressed by:

$$U(t) = K_p e(t) + K_i \int_0^t e(\tau) d\tau + K_d \frac{de(t)}{dt}$$

wherein, $\tau$ is timeslot, e(t) is error of the current time, and, K$_p$, K$_i$ and K$_d$ are proportional, integral and derivative gains, K$_p$, K$_i$ and K$_d$ are used for controlling the influence of proportional term, integral term and derivative term, a nonlinear modeling is conducted for the proposed endoscopic surgery system with automatic hydraulic monitoring function:

$$\frac{\frac{\partial u}{\partial t} + u \frac{\partial u}{\partial x}}{v \frac{\partial^2 u}{\partial x} - \frac{1}{\rho} \frac{x \partial p}{\partial x}} = F(x, t, Q_{in}(x, t), Q_{out}(x, t))$$

wherein, x is a spatial coordinate, t is time and v is kinematic viscosity; a multi-channel liquid flow situation, a coupling effect among channels, and channels influence each other by sharing liquid or having interactive flow paths are taken into account, a coupling term is introduced for modeling as below:

$$Q_{ij}(x,t) = f_{ij}(u_i(x,t), p_i(x,t), u_j(x,t), p_j((x,t)))$$

$Q_{ij}$ represents a rate of the liquid flowing out of channel i and into channel j, $F(x,t,Q_{in}(x,t),Q_{out}(x,t))$ represents a nonlinear control factor of the system, used for presenting a relationship between liquid flow and control input, wherein u(x,t) is flow rate, p(x,t) is pressure and ρ is fluid density. Relationship between liquid flow rate and hydraulic pressure is usually modeled by the following equation:

$$Q = A\mu$$

wherein, Q is liquid flow volume, A is cross-sectional area of flow, and μ is flow rate; the hydraulic sensor is considered to be introduced into the model, assuming that there is a nonlinear relationship between the hydraulic sensor output and the hydraulic intracavity pressure, it is expressed as follows:

$$P_{sensor} = f(P_{cavity})$$

wherein, $P_{sensor}$ is the pressure measured by the sensor, and $P_{cavity}$ is the actual intracavity pressure, f(•) represents a nonlinear sensor model; a state equation of the system is established, and the dynamic behavior of the liquid in cavity is expressed by:

$$\frac{dP_{cavity}}{dt} = \frac{1}{V}(Q_{in} - Q_{out})$$

wherein, $P_{cavity}$ is the intracavity pressure, $Q_{in}$ and $Q_{out}$ are perfusion rate and extraction rate of the liquid respectively; a goal of the control system is to make the intracavity pressure $P_{cavity}$ as close as possible to an expected value $P_{objective}$, thus minimizing the control error; for $$J(t) = \frac{1}{2}(P_{objective} - P(t))^2,$$

the goal of the control system is to minimize a control objective J(t) by adjusting the perfusion rate and extraction rate of the liquid, i.e., $Q_{in}(t)$ and $Q_{out}(t)$, it is expressed as minimizing the following objective function with a beam:

$$\begin{cases} \min_{Q_{in}(t), Q_{out}(t)} J(t) = \frac{1}{2}(P_{objective} - P(t))^2 \\ Q_{min} \leq Q_{in}(t) \leq Q_{max} \\ Q_{min} \leq Q_{out}(t) \leq Q_{max} \\ Q_{in}(t) = Q_{out}(t) \end{cases}$$

where $Q_{min}$ and $Q_{max}$ are minimum and maximum value of the liquid flow rate.

As an improvement of the endoscopic surgery system with automatic hydraulic monitoring function, two touch displays with the same functions are provided for use by physicians and nurses, respectively, the touch displays have functions of parameter setting, command input and displaying perfusion & extraction, pressure detection and intracavity image parameters on a same screen; the processor first determines whether operating conditions of the system are normal after receiving a start signal of the touch display or the endoscope accessory, wherein the operating conditions include whether system parameters are set correctly, whether conditions are met after identification by the hydraulic sensor, and whether original signals connected, operated and collected by the pressure measuring guide sheath and the electronic endoscope are normal; if the conditions are normal, the processor sends an instruction to the perfusion pump and the negative pressure pump, and the perfusion pump starts to act on the perfusion tube, and a perfusion pressure is formed in the perfusion tube; physiological saline is perfused into a body cavity through the electronic endoscope, meanwhile, the negative pressure pump works, allowing the collection container, the extraction tube and the pressure measuring guide sheath to form a vacuum negative pressure, and the physiological saline or other pollutants perfused into the body cavity are extracted out; and during the system's working process, the hydraulic sensor collects a liquid pressure in the body cavity through an independent pressure measuring channel on the pressure measuring guide path, and a pressure signal is converted into a voltage signal, and after being processed by hardware, it arrives the processor for analysis, and then an extraction force of the negative pressure pump is adjusted to keep the pressure in the body cavity at an expected set value.

The beneficial effects of the present application are as follows. Compared with the prior art, the invention provides a surgical endoscope system with integrated software and hardware and standardized configuration, which skillfully integrates a liquid perfusion device, a liquid extraction device, a liquid pressure monitoring and control device and a surgical endoscope. When the endoscope is employed for observation, the invention can control the liquid perfusion and extraction amount of endoscopic instruments, as well as the cavity liquid pressure in organs (such as renal pelvis, uterine cavity, biliary tract system, etc.), allowing for precise control of the intracavity pressure during operation. According to different requirements of endoscopic surgery, the configuration of the endoscope sheath is standardized to meet the requirements of adequate liquid circulation in various endoscopic operations, maintain a clear field of vision in cavity, and extract and remove samples from cavity. The real-time monitoring module calculates a state of the intracavity pressure based on real-time data obtained from the hydraulic sensor using intelligent PID control, and adjusts a perfusion and extraction speed of the liquid according to a given target pressure. The innovation lies in that the invention uses heuristic algorithm to construct exploration factors, and the exploration factors cooperate and adjust the position and speed through information exchange, thus establishing an information exchange model. Compared with the conventional algorithm, the invention is more inclined to the field of endoscopic surgery system with automatic hydraulic monitoring function, more emphases on the interaction of information, and has robustness and reliability. In addition, the invention employs PID algorithm. Different from the conventional method, the invention conducts nonlinear modeling for the proposed endoscopic surgery system with automatic hydraulic monitoring function, taking into account the multi-channel liquid flow situation, the coupling effect among channels, and the mutual influence between channels through shared liquid or interactive flow paths. By introducing the coupling term, the model is established, and the state equation of the system is established to describe the dynamic behavior of the liquid in cavity, and finally it is expressed as an objective function with constraints, so that the real-time calculation of big data is portable and the response and execution ability of the system provided by the application is accelerated.

In summary, the present application can not only meet the liquid flow, but also avoid the problem of various complications caused by excessive intracavity pressure, and can achieve safety warning. More importantly, the hydraulic sensor in the invention also has an intelligent identification function, which can guarantee the quality, sensing efficiency, sensing accuracy and use stability of the hydraulic sensor, thereby improving the safety of the invention. The invention can be applied to the urinary system, hepatobiliary system, uterine cavity system and other medical devices that need liquid as the medium for intracavitary surgery, and the application is very wide.

The advantages of the invention can be summarized as follows:

1. It provides a complete and easy-to-operate instrument solution for various endoscopic diagnosis and treatment technologies.

2. It has a liquid pressure detection system.

3. The parameters of perfusion extraction, pressure detection and intracavity image are displayed on the same screen.

4. It automatically adjusts the negative pressure extraction to reach the predetermined safe pressure value in cavity.

5. The perfusion flow can be adjusted and stopped by the surgeon, which is easy to obtain the ideal flow and reduce the operation steps.

6. The invention can solve the contradiction between the liquid perfusion amount and the intracavity pressure in clinical endoscopic surgery, achieve accurate matching of perfusion flow, flow rate and intracavity pressure, avoid complications, and provide a wider clinical application range and possibility.

7. The continuous water circulation of the invention can reduce the heat generated by holmium laser and other instruments.

8. The hydraulic sensor in the invention adopts the method of "actual measurement of impedance+key identification" to improve the stability of pressure hardware, thus improving the safety of device.

BRIEF DESCRIPTION OF THE DRAWINGS

In order to explain the technical solution of the embodiments of this application more clearly, the drawings described in the description of the embodiments of this application will be briefly introduced below. Obviously, the drawings in the present application and their accompanying detailed description are directed to merely exemplary embodiments of the application. For those of ordinary skill in this field, other drawings may be obtained according to these drawings without any creative effort.

It should be noted that the terms of "first" and "second" in the present application are merely used for descriptive purposes, and shall not be understood as indicating or implying their relative importance or implicitly indicating the number of indicated technical features. Therefore, the features defined as "first" and "second" can explicitly or implicitly include at least one of these features. In addition, the technical solutions of each embodiment can be combined with one another on the premise that it can be realized by those skilled in the art. When the combination of technical solutions is contradictory or impossible, it should be considered that the combination of technical solutions does not exist and is not within the protection scope of the present application.

Figure 1:
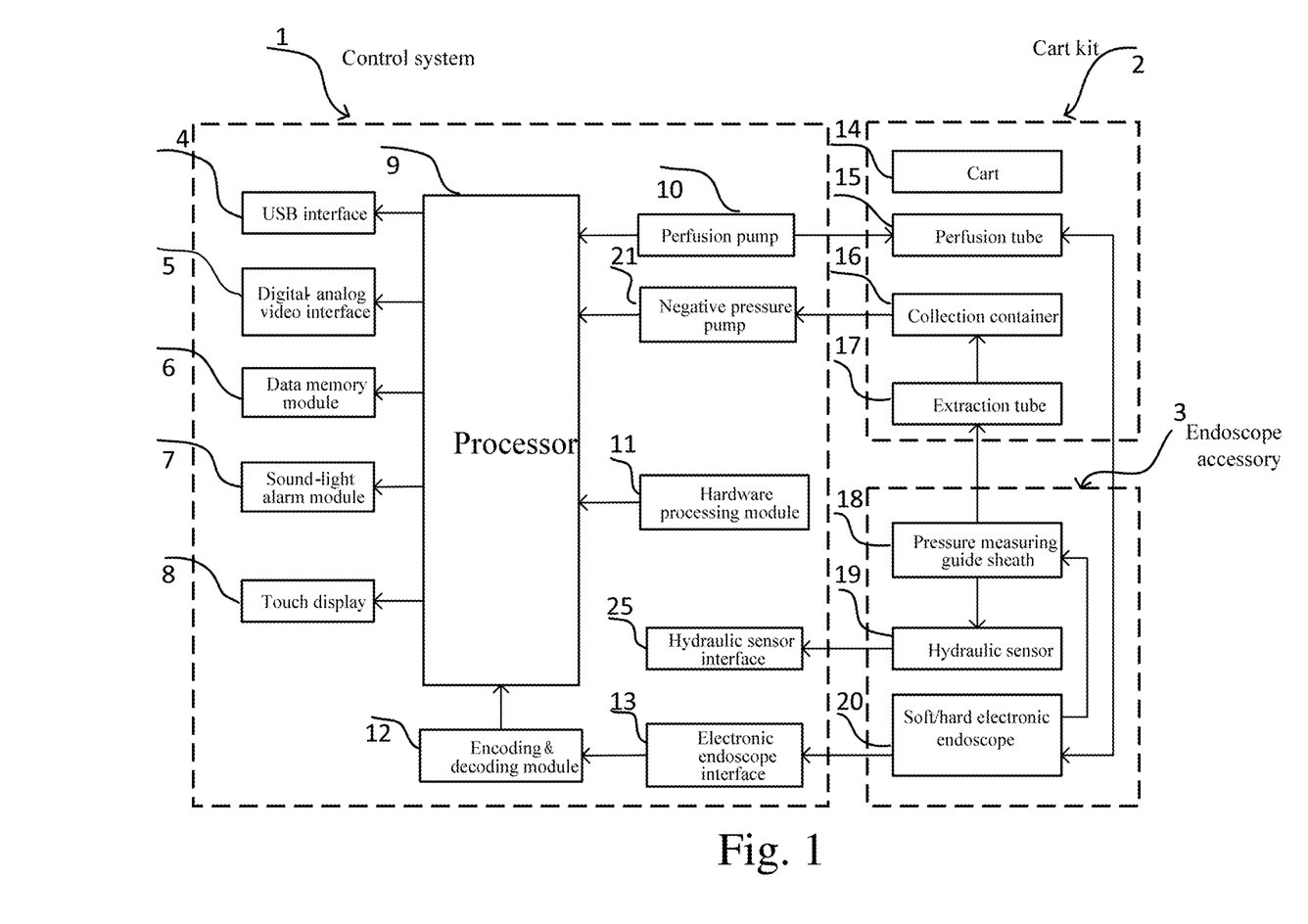
FIG. 1 is a structural diagram of the present application.

As shown in FIG. 1, the application provides an endoscopic surgery system with automatic hydraulic monitoring function, which includes a control system 1, a cart kit 2 and an endoscope accessory 3. The control system 1 includes a processor 9, and a USB interface 4, digital-analog video interface 5, data memory module 6, sound-light alarm module 7, touch display 8, encoding & decoding module 12, hardware processing module 11, perfusion pump 10 and negative pressure pump 21 connected with the processor 9. The cart kit 2 includes a cart 14, perfusion tube 15, collection container 16 and extraction tube 17. The endoscope accessory 3 includes a pressure measuring guide sheath 18, hydraulic sensor 19 and electronic endoscope 20. The perfusion pump 10 provides perfusion power for perfusion tube 15. The pressure measuring guide sheath 18 is connected with the input end of the extraction tube 17 and the piezometric tube of the hydraulic sensor 19. The electronic endoscope 20 is arranged in the pressure measuring guide sheath 18. The output end of the extraction tube 17 is connected with the collection container 16, the negative pressure pump 21 provides extraction power, and the hydraulic sensor 19 is a hydraulic sensor with recognition function.

The cart is a device for fixing, installing and arranging the control system 1, endoscope accessory 3, collection container 16, perfusion tube 15 and extraction tube 17. Moreover, the device has casters and can be moved to meet the needs of the operation site. The collection container 16 is used to collect waste liquid and other substances (such as stones) sucked out of the body. The perfusion tube 15 and extraction tube 17 are branches that provide water circulation and are made of silica gel. The hydraulic sensor 19 is an electronic component that collects internal pressure through liquid medium. The pressure measuring guide sheath 18 is a pressure measuring channel, instrument working channel and negative pressure extraction port, and it is an important part of medical endoscope system. In order to continuously and safely circulate the water, the invention introduces physiological saline into the body cavity by giving an execution signal of a certain magnitude to the perfusion pump 10 (the perfused physiological saline will increase the liquid pressure in cavity). And the hydraulic sensor 19 collects the pressure of liquid in the body cavity and feeds it back to the system (namely the processor 9). The processor 9 adjusts the extraction force of negative pressure pump 21 according to the feedback information (extraction will reduce the liquid pressure in cavity). The whole process is to obtain an expected relatively stable safe pressure in the body cavity.

Figure 2:
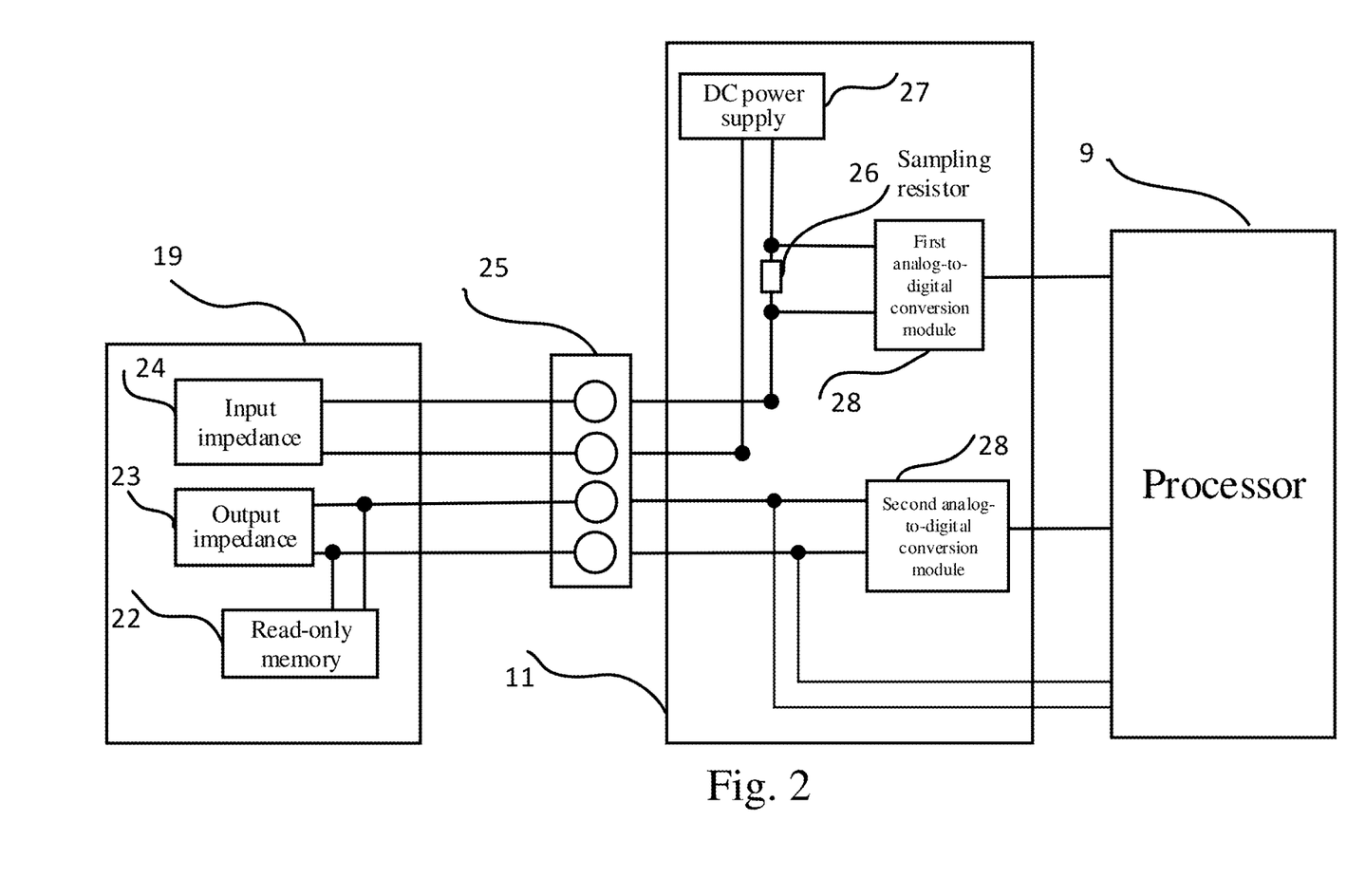
FIG. 2 is a structural diagram of hydraulic sensor identification of the present application.

As shown in FIG. 2, the hydraulic sensor 19 includes a programmable read-only memory 22, an output impedance 23 and an input impedance 24. The output impedance 23 is connected in parallel with the programmable read-only memory 22. Both the output impedance 23 and the input impedance 24 are detachably connected with the hydraulic sensor interface 25, the input impedance 24 branch is connected with DC power supply 27 via the hydraulic sensor interface 25 and sampling resistor 26. The sampling voltage of the sampling resistor 26 is output to the processor 9 through the first analog-to-digital conversion module 28. The output impedance branch is respectively connected with the second analog-to-digital conversion module and the processor 9 via the hydraulic sensor interface 25. The second analog-to-digital conversion module 28 outputs a signal to the processor 9. When the second analog-to-digital conversion module works, the branch connected to the processor 9 (without passing through the second analog-to-digital conversion module) is configured in a floating manner, i.e., it is equivalent to an open circuit.

That is, hydraulic sensor 19, hydraulic sensor interface 25, hardware processing module 11 and processor 9 cooperate to realize the identification means of "actual measurement of impedance+key identification", which includes two parts: actual measurement of impedance and key identification. The actual impedance measurement is determined by collecting the voltage of the sampling resistor 26 connected in series on the input impedance of the hydraulic sensor 1. The key identification is performed by sharing the hardware circuit of the input impedance 24 and carrying the programmable read-only memory 22 for parameter settings, and the identification period is selected by means of suspension control pin.

The memory contents of programmable read-only memory 22 include a preamble code, time, serial number, flag bit and checksum.

The hydraulic sensor 19 is an important component that enables this system to have automatic hydraulic monitoring and adjustment functions. Its identification functions include:

a) identification of line sequence errors and whether access is granted: when the hydraulic sensor 19 is not connected to the sensor interface 25, the sensor interface 25 is open-circuited, and a sampling voltage of the sampling resistor 26 is zero volts, thus it is determined that the hydraulic sensor 19 is not connected; when the hydraulic sensor 19 is connected to the sensor interface 25, a sampling voltage corresponding to the sampling resistor 26 voltage is obtained, thus it is determined that the hydraulic sensor 19 is connected and whether the line sequence of the connected hydraulic sensor is correct (different line sequences correspond to different sampling voltages);

b) identification of sensor matching: when the hydraulic sensor 19 is inserted into the system, the processor 9 reads the identification code on the hydraulic sensor 19 and compares it with the unique serial number (input when manufactured by the manufacturing company) stored in the programmable read-only memory, and if they are the same, they match, and if they are different, they do not match; specifically, when the hydraulic sensor 19 leaves the factory, the unique identification code is written into the programmable read-only memory 22, which corresponds to the serial number in the memory content; when the hydraulic sensor 19 is inserted into the device, the unique identification code is matched and identified, and it is matched to the manufacturing company; and c) identification of whether the sensor is used for the second time: a real-time clock circuit (with spare battery, the device can run normally when power is off) is arranged in the processor 9; when the hydraulic sensor 19 is inserted into the system, the processor 9 reads the flag bit in the programmable read-only memory 22 and determines whether the flag bit record is inserted for the first time; if yes, the current time is written into the programmable read-only memory 22; if no, the processor 9 reads the time stored in the programmable read-only memory 22 and compares it with the current time, and if it exceeds the time limit (invalid time), it is regarded as secondary use.

To sum up, the identification functions of the hydraulic sensor 19 in the present application mainly include: 1. whether there is a hardware error, such as whether the interface is connected or not, and whether there is a line sequence error; 2. identifying whether it is produced by its own company; 3. identifying whether the sensor is used for the second time. The hydraulic sensor 19 has the automatic identification function, therefore, it can ensure that the hydraulic sensor 19 used in the system has no hardware error and is not used for the second time, and it is produced by its own company (to prevent the hydraulic sensor 19 produced by other companies from being mismatched or unreliable in quality). This can ensure the quality, sensing efficiency, sensing accuracy and use stability of the hydraulic sensor 19, thereby improving the safety of the hydraulic monitoring system and ensuring the accurate realization of the hydraulic monitoring function of the hydraulic monitoring system.

The processor 9 is provided with a USB interface 4, digital-analog video interface 5, data memory module 6, sound-light alarm module 7, hardware processing module 11 and encoding & decoding module 12. The input end of the encoding & decoding module 12 is connected with electronic endoscope interface 13, and the input end of the hardware processing module 11 is connected with the sensor interface 25. The USB interface 4 is used for connecting printers, exporting and upgrading the system, and the analog-digital video interface 5 is used for connecting extended standard displays. The data memory module 6 is used to save system operation data. The sound-light alarm module 7 is a self-contained alarm system, which has three different levels. Specifically, low-priority alarm is an abnormal state when the device is not running, that is, errors detected when the system is not running, such as hardware initialization error, memory overflow, unreasonable parameter setting, and yellow light is normally open. Medium-priority alarm means that when the device is running, it is close to the critical value, that is, when the system is running, unacceptable abnormal signals are detected, such as the perfusion flow is close to the critical value and the pressure monitoring is close to the warning. This warning is an alarm, and the system is running normally, and the light form is yellow of 0.6 Hz. High-priority alarm is the fault state when the device is running, that is, the system detects an unacceptable signal, and then it is stopped; the light form is red of 1.6 Hz, and the alarm is given simultaneously in the form of two-color lights and sound.

The perfusion pump 10 is a device for perfusing liquid into human body by rolling, which can be adjusted by man-machine interaction, such as touch display 8, mechanical knobs and mechanical buttons. The negative pressure pump 21 is an extraction device for forming a vacuum negative pressure. The extraction device is fed back by the hydraulic sensor 19, processed by the hardware processing module 11 and the processor 9, and then sent a driving signal for adjustment. The encoding & decoding module 12 decodes the electronic endoscope 20, and the data is transmitted to the touch display 8 and the analog-digital video interface 5 through the processor 9.

The hardware processing module 11 converts analog signals collected by the hydraulic sensor 19 into digital signals, and then transmits them to the processor 9 for processing.

The electronic endoscope 20 is a soft electronic endoscope or hard electronic endoscope, and the electronic endoscope 20 is arranged in the pressure measuring guide sheath 18.

The electronic endoscope 20 is a catheter with a camera, and the electronic endoscope 20 communicates with the perfusion tube 15. The catheter channel can be arranged in other instruments (such as Holmium laser fiber) and liquid perfusion channels, and meanwhile transmit the original image signal to the control system. In order for the operator to directly control the start, stop and adjustment of the perfusion pump 10, the soft/hard electronic endoscope is provided with control buttons.

The processor 9 is an embedded processor, which runs the self-developed CFR (Core Full Register) embedded underlying software. The processor 9 is a micro processor, which is the control center of the whole system instruction. It has the characteristics of direct register drive, small running memory and fast response. The touch display 8 is an image display and man-machine interaction, which includes operation state, operation mode, pressure digital display, pressure adjustment, flow adjustment and image calibration.

The workflow of the invention is as follows. The operator sets the parameters of the system through the touch display 8, and the parameters include the pressure control value (target value), warning pressure value (alarm value), perfusion flow value, image adjustment value and system parameter value. Then the operator starts the system, there are two ways: one is the start signal from the touch display 8, and the other is the start signal from the endoscope accessory 3. After the processor 9 receives the start signal of the touch display 8 or endoscope accessory 3, it first determines the operating conditions of the system. The operating condition includes whether the system parameters are set correctly, whether the conditions are met after being identified by the hydraulic sensor 19, and whether the original signals connected, operated and collected by the pressure measuring guide sheath and electronic endoscope 20 are normal (the identification function is the condition for the hydraulic sensor 19 to normally enter the system, and it will switch to the working mode after normal entry, and the recognition function will not function in this state). Secondly, when the conditions are normal, the processor 9 sends instructions to the perfusion pump 10 and the negative pressure pump 21, and the perfusion pump 10 starts to act on the perfusion tube 15, and the perfusion pressure is formed in the perfusion tube 15. Normal saline is perfused into cavity through the electronic endoscope 20 (the electronic endoscope 20 can collect image signals and transmit them to the encoding & decoding module 12 controlled by the processor 9 via the electronic endoscope interface 13. Then a clear image is displayed on the touch display 8, so as to maintain a clear field of vision in cavity). Meanwhile, the negative pressure pump 21 starts to work, which is a vacuum negative pressure source, and enables the collection container 16, the extraction tube 17 and the pressure measuring guide sheath 18 to form a vacuum negative pressure to suck out the physiological saline perfused into the body cavity or other pollutants (such as stones and pathological tissues). If the conditions are not met, the system cannot be started. Finally, during the working process of the system, the hydraulic sensor 19 collects the liquid pressure in the body cavity (using liquid as the medium) through a separate pressure measuring channel on the pressure measuring guide path 18. The pressure signal is converted into a voltage signal via the pressure resistance bridge, and then passes through the sensor interface 25 and hardware processing module 11. After the signal arrives the processor 9 for analysis, the extraction force of the negative pressure pump 21 is adjusted to keep the pressure in the body cavity at an expected set value.

Specifically, pressure change of a cavity liquid is expressed by the following difference equation:

$$P(t+1) = P(t) + \Delta P_{in} - \Delta P_{out}$$

wherein, $\Delta P_{in}$ is the pressure change caused by liquid perfusion, $\Delta P_{out}$ is the pressure change caused by liquid extraction, $P(t)$ represents a pressure at time t, and $P(t+1)$ represents a pressure at time $t(t+1)$; suppose there are an exploration factors, and a position and speed of each exploration factor represent a parameter value of a control strategy, in each iteration, the position and speed of each exploration factor are updated, and a fitness value is calculated; wherein a parameter of the control strategy is represented by d dimensions, each dimension corresponds to a control parameter, and the control strategy is expressed as d dimension vector X, where $X=(X_1, X_2, \ldots, X_d)$, $X_1$ represents a value of the first dimension parameter, $X_2$ represents a value of the second dimension parameter, and $X_d$ represents a value of the $d_{th}$ dimension parameter, and an objective function $H(X)$ is defined and used for evaluating performance of each exploration factor, $H(X)$ is expressed as follows:

$$H(X) = w_1\epsilon(X) + w_2 k(X_{in} + X_{out})$$

$\epsilon$ represents pressure control error, $X_{in}$ represents liquid perfusion speed parameter, $X_{out}$ represents liquid extraction speed parameter, $k(X_{in}+X_{out})$ represents energy consumption, that is, the energy required for liquid flow caused by the control strategy, k is a constant related to the energy consumption per fluid speed unit, $w_1$ and $w_2$ are parameters for balancing weight of the pressure control error and the energy consumption; a fitness function $A(X)$ is defined as $H(X)$, and the objective function includes pressure control error and energy consumption: $A(X)=-H(X)$, and a position update model of each exploration factor i is expressed by:

$$X_i(t+1) = X_i(t) + \Delta X_i(t+1)$$

$X_i(t)$ represents the position of the exploration factor i at time t, and is a d dimension vector; $\Delta X_i(t+1)$ represents a position variance of the exploration factor i at time t+1, and the speed update model of each exploration factor i is expressed by:

$$V_i(t+1) = V_i(t) + \Delta V_i(t+1)$$

$V_i(t)$ represents a speed of the exploration factor i at time t, corresponds to the position update, and is a d dimensional vector; $\Delta V_i(t+1)$ represents a speed variance of the exploration factor i at time t+1; the position and speed of the exploration factors i are coordinated and adjusted through information exchange, and the information exchange is expressed by the following model:

$$\Delta X_i(t+1) = H_1(X_i(t), X_{neighbor_i}(t), t) \int_{T_0}^{T^*} X_i(t) X_{neighbor_i}(t+l) dt +$$

$$- \sum_{i=1}^{N} pr(X_i(t)) \log(pr(X_i(t))) H_2(X_i(t), t)$$

$$\Delta V_i(t+1) =$$

$$\gamma H_3(X_i(t), V_i(t), X_{neighbor_i}(t), t) + H_4(X_i(t), V_i(t), t) \int_{T_0}^{T^*} X_i(t) V_i(t+l) dt$$

$X_{neighbor_i}(t)$ represents the position of the neighbor exploration factor i at time t, $\Delta X_i(t+1)$ and $\Delta V_i(t+1)$ are variations of position and speed, used for updating the position and speed respectively, $\gamma$ is an adjustment parameter, and affects weight of the information exchange, $T_0$ represents an initial time of statistics, $T^*$ represents an ending time of statistics, $H_1(X_i(t), X_{neighbor_i}(t),t)$ and $H_2(X_i(t),t)$ are information exchange functions of the neighboring exploration factor, used for adjusting the position, $H_3(X_i(t),V_i(t),X_{neighbor_i}(t),t)$ and $H_4(X_1(t),V_i(t),t)$ are information exchange functions of the neighboring exploration factor, used for adjusting the speed, to indicate the information exchange function with the adjacent exploration factor, l is lag time, and pr is a probability function.

Specifically, a dynamic behavior of liquid perfusion and extraction and a response of pressure are expressed by the following formula:

$$\dot{P} = \frac{Q_{in}(t) - Q_{out}(t)}{V}$$

wherein, $\dot{P}(t)$ represents a change rate of pressure, $Q_{in}(t)$ represents a liquid perfusion rate at time t, $Q_{out}(t)$ represents a liquid extraction rate at time t, V represents a volume of the cavity, and the objective function J(t) is defined as:

$$J(t) = \frac{1}{2}(P_{objective} - P(t))^2$$

it represents a performance index pursued by the system, the objective function is the difference between the intracavity pressure and the target pressure, i.e., P(t) is the pressure at time t, $P_{objective}$ is the expected target pressure, and an output of a PID control algorithm is expressed by:

$$U(t) = K_p e(t) + K_i \int_0^t e(\tau) d\tau + K_d \frac{de(t)}{dt}$$

wherein, $\tau$ is timeslot, e(t) is error of the current time, and, $K_p$, $K_i$ and $K_d$ are proportional, integral and derivative gains, $K_p$, $K_i$ and $K_d$ are used for controlling the influence of proportional term, integral term and derivative term, a nonlinear modeling is conducted for the proposed endoscopic surgery system with automatic hydraulic monitoring function:

$$\frac{\frac{\partial u}{\partial t} + u \frac{\partial u}{\partial x}}{v \frac{\partial^2 u}{\partial x} - \frac{1}{\rho} \frac{\partial p}{\partial x}} = F(x, t, Q_{in}(x,t), Q_{out}(x,t))$$

wherein, x is a spatial coordinate, t is time and v is kinematic viscosity; a multi-channel liquid flow situation, a coupling effect among channels, and channels influence each other by sharing liquid or having interactive flow paths are taken into account, a coupling term is introduced for modeling as below:

$$Q_{ij}(x,t) = f_{ij}(u_i(x,t), p_i(x,t), u_i(x,t), p_i((x,t)))$$

$Q_{ij}$ represents a rate of the liquid flowing out of channel i and into channel j, $F(x,t,Q_{in}(x,t),Q_{out}(x,t))$ represents a nonlinear control factor of the system, used for presenting a relationship between liquid flow and control input, wherein u(x,t) is flow rate, p(x,t) is pressure and $\rho$ is fluid density. Relationship between liquid flow rate and hydraulic pressure is usually modeled by the following equation:

$$Q = A\mu$$

wherein, Q is liquid flow volume, A is cross-sectional area of flow, and $\mu$ is flow rate; the hydraulic sensor is considered to be introduced into the model, assuming that there is a nonlinear relationship between the hydraulic sensor output and the hydraulic intracavity pressure, it is expressed as follows:

$$P_{sensor} = f(P_{cavity})$$

wherein, $P_{sensor}$ is the pressure measured by the sensor, and $P_{cavity}$ is the actual intracavity pressure, f(•) represents a nonlinear sensor model; a state equation of the system is established, and the dynamic behavior of the liquid in cavity is expressed by:

$$\frac{dP_{cavity}}{dt} = \frac{1}{V}(Q_{in} - Q_{out})$$

wherein, $P_{cavity}$ is the intracavity pressure, $Q_{in}$ and $Q_{out}$ are perfusion rate and extraction rate of the liquid respectively; a goal of the control system is to make the intracavity pressure $P_{cavity}$ as close as possible to an expected value $P_{objective}$, thus minimizing the control error; for $$J(t) = \frac{1}{2}(P_{objective} - P(t))^2,$$

the goal of the control system is to minimize a control objective J(t) by adjusting the perfusion rate and extraction rate of the liquid, i.e., $Q_{in}(t)$ and $Q_{out}(t)$, it is expressed as minimizing the following objective function with a beam:

$$\begin{cases} \min_{Q_{in}(t), Q_{out}(t)} J(t) = \frac{1}{2}(P_{objective} - P(t))^2 \\ Q_{min} \leq Q_{in}(t) \leq Q_{max} \\ Q_{min} \leq Q_{out}(t) \leq Q_{max} \\ Q_{in}(t) = Q_{out}(t) \end{cases}$$

where $Q_{min}$ and $Q_{max}$ are minimum and maximum value of the liquid flow rate.

In summary, the invention integrates the following functions: liquid supply, liquid pressure detection in cavity, vacuum negative pressure extraction, endoscopic image, image processing and image display capability. According to different endoscopes, while intelligently monitoring and controlling the liquid pressure in organs (such as renal pelvis, uterine cavity, biliary tract, etc.), the invention provides continuous, stable and optimal liquid circulation amount, directly observes the situation in the cavity, and extract and removes pathological samples from the cavity.

The beneficial effects of the present application are as follows. Compared with the prior art, the invention provides a surgical endoscope system with integrated software and hardware and standardized configuration, which skillfully integrates a liquid perfusion device, a liquid extraction device, a liquid pressure monitoring and control device and a surgical endoscope. When the endoscope is employed for observation, the invention can control the liquid perfusion and extraction amount of endoscopic instruments, as well as the cavity liquid pressure in organs (such as renal pelvis, uterine cavity, biliary tract system, etc.), allowing for precise control of the intracavity pressure during operation. According to different requirements of endoscopic surgery, the configuration of the endoscope sheath is standardized to meet the requirements of adequate liquid circulation in various endoscopic operations, maintain a clear field of vision in cavity, and extract and remove samples from cavity. The real-time monitoring module calculates a state of the intracavity pressure based on real-time data obtained from the hydraulic sensor using intelligent PID control, and adjusts a perfusion and extraction speed of the liquid according to a given target pressure. The innovation lies in that the invention uses heuristic algorithm to construct exploration factors, and the exploration factors cooperate and adjust the position and speed through information exchange, thus establishing an information exchange model. Compared with the conventional algorithm, the invention is more inclined to the field of endoscopic surgery system with automatic hydraulic monitoring function, more emphases on the interaction of information, and has robustness and reliability. In addition, the invention employs PID algorithm. Different from the conventional method, the invention conducts nonlinear modeling for the proposed endoscopic surgery system with automatic hydraulic monitoring function, taking into account the multi-channel liquid flow situation, the coupling effect among channels, and the mutual influence between channels through shared liquid or interactive flow paths. By introducing the coupling term, the model is established, and the state equation of the system is established to describe the dynamic behavior of the liquid in cavity, and finally it is expressed as an objective function with constraints, so that the real-time calculation of big data is portable and the response and execution ability of the system provided by the application is accelerated.

In summary, the present application can not only meet the liquid flow, but also avoid the problem of various complications caused by excessive intracavity pressure, and can achieve safety warning. More importantly, the hydraulic sensor in the invention also has an intelligent identification function, which can guarantee the quality, sensing efficiency, sensing accuracy and use stability of the hydraulic sensor, thereby improving the safety of the invention. The invention can be applied to the urinary system, hepatobiliary system, uterine cavity system and other medical devices that need liquid as the medium for intracavitary surgery, and the application is very wide.

The advantages of the invention can be summarized as follows:

1. It provides a complete and easy-to-operate instrument solution for various endoscopic diagnosis and treatment technologies.
2. It has a liquid pressure detection system.
3. The parameters of perfusion extraction, pressure detection and intracavity image are displayed on the same screen.
4. It automatically adjusts the negative pressure extraction to reach the predetermined safe pressure value in cavity.
5. The perfusion flow can be adjusted and stopped by the surgeon, which is easy to obtain the ideal flow and reduce the operation steps.
6. The invention can solve the contradiction between the liquid perfusion amount and the intracavity pressure in clinical endoscopic surgery, achieve accurate matching of perfusion flow, flow rate and intracavity pressure, avoid complications, and provide a wider clinical application range and possibility.
7. The continuous water circulation of the invention can reduce the heat generated by holmium laser and other instruments.
8. The hydraulic sensor in the invention adopts the method of "actual measurement of impedance+key identification" to improve the stability of pressure hardware, thus improving the safety of device.

The above are preferred embodiments of the present application, and other designs and processing techniques with the same or similar principle and basic structure as these embodiments and similar appearance are all within the protection scope of the present application. In addition, although some specific terms are used in this specification, these terms are only for the convenience of description and do not constitute any limitations on the present application.

What is claimed is:

1. An endoscopic surgery system with automatic hydraulic monitoring function, comprising a control system, a cart kit and an endoscope accessory; the control system comprises a processor, and a touch display, a perfusion pump and a negative pressure pump connected with the processor; the cart kit comprises a cart, a perfusion tube and a extraction tube; the endoscope accessory comprises a pressure measuring guide sheath, a hydraulic sensor and an electronic endoscope; the hydraulic sensor is a sensor with a recognition function; the perfusion tube is powered by the perfusion pump, and the perfusion tube is connected with a perfusion channel of the electronic endoscope; the electronic endoscope is arranged in the pressure measuring guide sheath, and the pressure measuring guide sheath is connected with an end of the extraction tube and a piezometric tube of the hydraulic sensor, another end of the extraction tube is provided with a extraction power by the negative pressure pump, and the hydraulic sensor is connected with the processor via the hydraulic sensor interface and the hardware processing module in turn;

the processor is provided with a USB interface, a digital-analog video interface, a real-time monitoring module, a data memory module, a sound-light alarm module, a hardware processing module and an encoding & decoding module; wherein an input end of the encoding & decoding module is connected with an electronic endoscope interface, an input end of the electronic endoscope interface is connected with the electronic endoscope, and an output end of the encoding & decoding module is connected with the processor; wherein the real-time monitoring module is used for monitoring the pressure of liquid in an organ in real time and providing data to the control system, so as to realize accurate control of intracavity pressure during operation, and the real-time monitoring module comprises a plurality of high-precision hydraulic sensors, these sensors are arranged in the organ and close to an operation area so as to measure the pressure of liquid in the organ; the hydraulic sensor transmits real-time pressure data to the control system through a data line connected to the control system or a wireless communication mode, calculates a state of the intracavity pressure based on real-time data obtained from the hydraulic sensor using intelligent PID control, and adjusts a perfusion and extraction speed of the liquid according to a given target pressure, so as to maintain the intracavity pressure in a safe range, details are as follows:

pressure change of a cavity liquid is expressed by the following difference equation:

$$P(t+1) = P(t) + \Delta P_{in} - \Delta P_{out}$$

wherein, $\Delta P_{in}$ is the pressure change caused by liquid perfusion, $\Delta P_{out}$ is the pressure change caused by liquid extraction, P(t) represents a pressure at time t, and P(t+1) represents a pressure at time t(t+1); suppose there are an exploration factors, and a position and speed of each exploration factor represent a parameter value of a control strategy, in each iteration, the position and speed of each exploration factor are updated, and a fitness value is calculated; wherein a parameter of the control strategy is represented by d dimensions, each dimension corresponds to a control parameter, and the control strategy is expressed as d dimension vector X, where $X=(X_1, X_2, \ldots, X_d)$, $X_1$ represents a value of the first dimension parameter, $X_2$ represents a value of the second dimension parameter, and $X_d$ represents a value of the $d_{th}$ dimension parameter, and an objective function H(X) is defined and used for evaluating performance of each exploration factor, H(X) is expressed as follows:

$$H(X) = w_1 \epsilon(X) + w_2 k(X_{in} + X_{out})$$

$\epsilon$ represents pressure control error, $X_{in}$ represents liquid perfusion speed parameter, $X_{out}$ represents liquid extraction speed parameter, $k(X_{in}+X_{out})$ represents energy consumption, that is, the energy required for liquid flow caused by the control strategy, k is a constant related to the energy consumption per fluid speed unit, $w_1$ and $w_2$ are parameters for balancing weight of the pressure control error and the energy consumption; a fitness function A(X) is defined as H(X), and the objective function comprises pressure control error and energy consumption: $A(X)=-H(X)$, and a position update model of each exploration factor i is expressed by:

$$X_i(t+1) = X_i(t) + \Delta X_i(t+1)$$

$X_i(t)$ represents the position of the exploration factor i at time t, and is a d dimension vector; $\Delta X_i(t+1)$ represents a position variance of the exploration factor i at time t+1, and the speed update model of each exploration factor i is expressed by:

$$V_i(t+1) = V_i(t) + \Delta V_i(t+1)$$

$V_i(t)$ represents a speed of the exploration factor i at time t, corresponds to the position update, and is a d dimensional vector; $\nabla V_i(t+1)$ represents a speed variance of the exploration factor i at time t+1; the position and speed of the exploration factors i are coordinated and adjusted through information exchange, and the information exchange is expressed by the following model:

$$\Delta X_i(t+1) = H_1\big(X_i(t), X_{neighbor_i}(t), t\big) \int_{T_0}^{T^*} X_i(t) X_{neighbor_i}(t+l) dt +$$
$$- \sum_{i=1}^{N} pr(X_i(t)) \log(pr(X_i(t))) H_2(X_i(t), t)$$

$$\Delta V_i(t+1) =$$
$$\gamma H_3\big(X_i(t), V_i(t), X_{neighbor_i}(t), t\big) + H_4(X_i(t), V_i(t), t) \int_{T_0}^{T^*} X_i(t) V_i(t+l) dt$$

$X_{neighbor_i}(t)$ represents the position of the neighbor exploration factor i at time t, $\Delta X_i(t+1)$ and $\Delta V_i(t+1)$ are variations of position and speed, used for updating the position and speed respectively, $\gamma$ is an adjustment parameter, and affects weight of the information exchange, $T_0$ represents an initial time of statistics, $T^*$ represents an ending time of statistics, $H_1(X_i(t), X_{neighbor_i}(t),t)$ and $H_2(X_i(t),t)$ are information exchange functions of the neighboring exploration factor, used for adjusting the position, $H_3(X_i(t),V_i(t),X_{neighbor_i}(t),t)$ and $H_4(X_i(t),V_i(t),t)$ are information exchange functions of the neighboring exploration factor, used for adjusting the speed, to indicate the information exchange function with the adjacent exploration factor, l is lag time, and pr is a probability function.

2. The endoscopic surgery system with automatic hydraulic monitoring function of claim 1, wherein the hydraulic sensor comprises a programmable read-only memory, an output impedance and an input impedance; the output impedance is connected in parallel with the programmable read-only memory, and both the output impedance and the input impedance are detachably connected with a hydraulic sensor interface; the input impedance is connected with DC power supply via the hydraulic sensor interface and a sampling resistor, and a sampling resistor voltage outputs signals to the processor through a first analog-to-digital conversion module; the output impedance is connected with a second analog-to-digital conversion module and the processor via the hydraulic sensor interface, and the second analog-to-digital conversion module outputs signals to the processor.

3. The endoscopic surgery system with automatic hydraulic monitoring function of claim 2, wherein a memory content of the programmable read-only memory comprises a preamble code, time, serial number, flag bit and checksum; the preamble code is a frame header of the memory content, the time is the first recorded time, the serial number is an unique identification code of the hydraulic sensor, the flag bit is an insertion state of the recorded hydraulic sensor, and the function of the checksum is to verify the completeness of the preamble code, time, serial number and flag bit.

4. The endoscopic surgery system with automatic hydraulic monitoring function of claim 2, wherein an identification function of the hydraulic sensor comprises:
   a) identification of line sequence errors and whether access is granted: when the hydraulic sensor is not connected to the sensor interface, the sensor interface is open-circuited, and a sampling voltage of the sampling resistor is zero volts, thus it is determined that the hydraulic sensor is not connected; when the hydraulic sensor is connected to the sensor interface, a sampling voltage corresponding to the sampling resistor voltage is obtained, thus it is determined that the hydraulic sensor is connected and whether the line sequence of the connected hydraulic sensor is correct;
   b) identification of sensor matching: when the hydraulic sensor is inserted into the sensor interface, the processor compares the identification code in the system with the unique serial number stored in the programmable read-only memory, and if they are the same, they match, and if they are different, they do not match; and
   c) identification of whether the sensor is used for the second time: a real-time clock circuit is arranged in the processor; when the hydraulic sensor is inserted into the sensor interface, the processor reads the flag bit in the programmable read-only memory and determines whether the flag bit record is inserted for the first time; if yes, the current time is written into the programmable read-only memory and the status of the flag bit is changed; if no, the processor reads the time stored in the programmable read-only memory and compares it with the current time, and if it exceeds the time limit, it is regarded as secondary use.

5. The endoscopic surgery system with automatic hydraulic monitoring function of claim 1, wherein the electronic endoscope is a soft electronic endoscope or a hard electronic endoscope, and the electronic endoscope is a catheter with a camera.

6. The endoscopic surgery system with automatic hydraulic monitoring function of claim 5, wherein the cart kit further comprises a collection container, and another end of the extraction tube is connected with the collection container.

7. The endoscopic surgery system with automatic hydraulic monitoring function of claim 1, wherein the processor is an embedded processor and runs CFR (Core Full Register) embedded underlying software.

8. The endoscopic surgery system with automatic hydraulic monitoring function of claim 7, wherein a dynamic behavior of liquid perfusion and extraction and a response of pressure are expressed by the following formula:

$$\dot{P} = \frac{Q_{in}(t) - Q_{out}(t)}{V}$$

wherein, $\dot{P}(t)$ represents a change rate of pressure, $Q_{in}(t)$ represents a liquid perfusion rate at time t, $Q_{out}(t)$ represents a liquid extraction rate at time t, V represents a volume of the cavity, and the objective function J(t) is defined as:

$$J(t) = \frac{1}{2}(P_{objective} - P(t))^2$$

it represents a performance index pursued by the system, the objective function is the difference between the intracavity pressure and the target pressure, i.e., P(t) is the pressure at time t, $P_{objective}$ is the expected target pressure, and an output of a PID control algorithm is expressed by:

$$U(t) = K_p e(t) + K_i \int_0^t e(\tau)d\tau + K_d \frac{de(t)}{dt}$$

wherein, $\tau$ is timeslot, e(t) is error of the current time, and, $K_p$, $K_i$ and $K_d$ are proportional, integral and derivative gains, $K_p$, $K_i$ and $K_d$ are used for controlling the influence of proportional term, integral term and derivative term, a nonlinear modeling is conducted for the proposed endoscopic surgery system with automatic hydraulic monitoring function:

$$\frac{\frac{\partial u}{\partial t} + u \frac{\partial u}{\partial x}}{v \frac{\partial^2 u}{\partial x} - \frac{1}{\rho}\frac{\partial p}{\partial x}} = F(x, t, Q_{in}(x, t), Q_{out}(x, t))$$

wherein, x is a spatial coordinate, t is time and v is kinematic viscosity; a multi-channel liquid flow situation, a coupling effect among channels, and channels influence each other by sharing liquid or having interactive flow paths are taken into account, a coupling term is introduced for modeling as below:

$$Q_{ij}(x,t)=f_{ij}(u_i(x,t),p_i(x,t),u_j(x,t),p_j((x,t)))$$

$Q_{ij}$ represents a rate of the liquid flowing out of channel i and into channel j, $F(x,t,Q_{in}(x,t),Q_{out}(x,t))$ represents a nonlinear control factor of the system, used for presenting a relationship between liquid flow and control input, wherein u(x,t) is flow rate, p(x,t) is pressure and $\rho$ is fluid density, Relationship between liquid flow rate and hydraulic pressure is usually modeled by the following equation:

$$Q=A\mu$$

wherein, Q is liquid flow volume, A is cross-sectional area of flow, and $\mu$ is flow rate; the hydraulic sensor is considered to be introduced into the model, assuming that there is a nonlinear relationship between the hydraulic sensor output and the hydraulic intracavity pressure, it is expressed as follows:

$$P_{sensor}=f(P_{cavity})$$

wherein, $P_{sensor}$ is the pressure measured by the sensor, and $P_{cavity}$ is the actual intracavity pressure, f(•) represents a nonlinear sensor model; a state equation of the system is established, and the dynamic behavior of the liquid in cavity is expressed by:

$$\frac{dP_{cavity}}{dt} = \frac{1}{V}(Q_{in} - Q_{out})$$

wherein, $P_{cavity}$ is the intracavity pressure, $Q_{in}$ and $Q_{out}$ are perfusion rate and extraction rate of the liquid respectively; a goal of the control system is to make the intracavity pressure $P_{cavity}$ as close as possible to an expected value $P_{objective}$, thus minimizing the control error; for $$J(t) = \frac{1}{2}(P_{objective} - P(t))^2,$$

the goal of the control system is to minimize a control objective J(t) by adjusting the perfusion rate and extraction rate of the liquid, i.e., $Q_{in}(t)$ and $Q_{out}(t)$, it is expressed as minimizing the following objective function with a beam:

$$\begin{cases} \min_{Q_{in}(t),Q_{out}(t)} J(t) = \frac{1}{2}(P_{objective} - P(t))^2 \\ Q_{min} \leq Q_{in}(t) \leq Q_{max} \\ Q_{min} \leq Q_{out}(t) \leq Q_{max} \\ Q_{in}(t) = Q_{out}(t) \end{cases}$$

where $Q_{min}$ and $Q_{max}$ are minimum and maximum value of the liquid flow rate.

9. The endoscopic surgery system with automatic hydraulic monitoring function of claim 1, wherein two touch displays with the same functions are provided for use by physicians and nurses, respectively, the touch displays have functions of parameter setting, command input and displaying perfusion & extraction, pressure detection and intracavity image parameters on a same screen; the processor first determines whether operating conditions of the system are normal after receiving a start signal of the touch display or the endoscope accessory, wherein the operating conditions include whether system parameters are set correctly, whether conditions are met after identification by the hydraulic sensor, and whether original signals connected, operated and collected by the pressure measuring guide sheath and the electronic endoscope are normal; if the conditions are normal, the processor sends an instruction to the perfusion pump and the negative pressure pump, and the perfusion pump starts to act on the perfusion tube, and a perfusion pressure is formed in the perfusion tube; physiological saline is perfused into a body cavity through the electronic endoscope, meanwhile, the negative pressure pump works, allowing the collection container, the extraction tube and the pressure measuring guide sheath to form a vacuum negative pressure, and the physiological saline or other pollutants perfused into the body cavity are extracted out; and during the system's working process, the hydraulic sensor collects a liquid pressure in the body cavity through an independent pressure measuring channel on the pressure measuring guide path, and a pressure signal is converted into a voltage signal, and after being processed by hardware, it arrives the processor for analysis, and then an extraction force of the negative pressure pump is adjusted to keep the pressure in the body cavity at an expected set value.

\* \* \* \* \*